(12) United States Patent
Singer

(10) Patent No.: US 7,270,672 B1
(45) Date of Patent: Sep. 18, 2007

(54) ROD FOR TRANSFERRING AND TIGHTENING KNOTTED SUTURE INTO PATIENT'S BODY

(76) Inventor: Adam Joel Singer, 17 Hacienda Rd., Bell Canyon, CA (US) 91307

( * ) Notice: Subject to any disclaimer, the term of this patent is extended or adjusted under 35 U.S.C. 154(b) by 414 days.

(21) Appl. No.: 11/055,871

(22) Filed: Feb. 11, 2005

(51) Int. Cl.
- A61B 17/04 (2006.01)
- A61B 17/06 (2006.01)
- A61B 17/10 (2006.01)
- B65A 59/00 (2006.01)
- D05B 35/00 (2006.01)

(52) U.S. Cl. .............. 606/148; 606/222; 606/139; 606/144; 606/138; 606/223; 112/270; 112/136

(58) Field of Classification Search ............... 606/139, 606/144, 148, 222, 223; 112/270, 136
See application file for complete search history.

(56) References Cited

U.S. PATENT DOCUMENTS

| | | | |
|---|---|---|---|
| 2,595,086 A | 4/1952 | Larzelere | |
| 3,871,379 A | 3/1975 | Clarke | |
| 4,574,805 A * | 3/1986 | Lerner | 606/148 |
| 4,602,635 A | 7/1986 | Mulhollan et al. | |
| 4,961,741 A | 10/1990 | Hayhurst | |
| 5,084,058 A | 1/1992 | Li | |
| 5,133,723 A | 7/1992 | Li et al. | |
| 5,163,946 A | 11/1992 | Li | |
| 5,176,691 A | 1/1993 | Pierce | |
| 5,192,287 A | 3/1993 | Fournier et al. | |
| 5,201,744 A | 4/1993 | Jones | |
| 5,217,471 A | 6/1993 | Burkhart | |
| 5,234,444 A | 8/1993 | Christoudias | |
| 5,269,791 A | 12/1993 | Mayzels et al. | |
| 5,292,327 A | 3/1994 | Dodd et al. | |
| 5,324,298 A | 6/1994 | Phillips et al. | |
| 5,397,326 A | 3/1995 | Magnum | |
| 5,403,330 A | 4/1995 | Tuason | |
| 5,423,837 A | 6/1995 | Mericle et al. | |
| 5,549,618 A | 8/1996 | Fleenor et al. | |
| 5,693,061 A | 12/1997 | Pierce et al. | |
| 5,741,280 A | 4/1998 | Fleenor | |

(Continued)

Primary Examiner—Anhtuan T. Nguyen
Assistant Examiner—Amy T. Lang

(57) ABSTRACT

A knot placer has a rod (10) connecting a handle end (11) to a working end (12). The working end (12) has a closed leg eyelet (15) and a slit leg eyelet (16). A slidable knot (27), formed from a pair of ends of surgical suture (25*a*) and (25*b*) is used to join a patient's tissue. The knot (27) can be transferred through an access port (21) and tightened at a surgical site (26) by threading each respective suture end (25*a*) and (25*b*) into each eyelet (15) and (16), grasping the handle end (11), and pushing the slidable knot (27) to the surgical site (26) during an endoscopic surgery. Subsequently, the knot placer can be pulled out of the access port (21), and the slit eyelet (16) can release its respective suture end (25*a*) or (25*b*) through the slit (19). Another slidable knot (27) can be tied. The respective suture end (25*a*) or (25*b*) can be replaced into the slit eyelet (18) through the slit (19) so that the knot placer can be used to transfer and tighten another slidable knot (27) at the internal surgical site (26). Thus, the knot placer can be used for transferring and tightening a plurality of slidable knots (27) to join the patient's tissues at the internal surgical site (26) one at a time.

11 Claims, 4 Drawing Sheets

U.S. PATENT DOCUMENTS

| | | |
|---|---|---|
| 5,752,964 A | 5/1998 | Mericle |
| 5,797,929 A | 8/1998 | Andreas et al. |
| 5,961,530 A * | 10/1999 | Moore et al. ............... 606/148 |
| 6,045,561 A | 4/2000 | Marshall et al. |
| 6,221,084 B1 | 4/2001 | Fleenor |
| 6,258,106 B1 | 7/2001 | Leonard |
| 6,322,570 B1 * | 11/2001 | Matsutani et al. .......... 606/145 |
| 2003/0216752 A1 * | 11/2003 | Williamson et al. ........ 606/139 |

* cited by examiner

ROD FOR TRANSFERRING AND TIGHTENING KNOTTED SUTURE INTO PATIENT'S BODY

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of Invention

The present invention relates generally to a surgical knot instrument, specifically to a device that transfers and tightens a knotted suture from outside to inside a patient's body during a surgery in order to attach severed and non-severed internal tissues.

2. Prior Art

Placing a surgical knot of a suture during an endoscopic procedure such as laparoscopy, pelviscopy, thoracoscopy, and arthroscopy can be difficult because access to the surgical site must be obtained through a number of hollow entry-exit access tubes, called "access ports" in the medical field, each inserted into a patient's body through a small incision in lieu of a traditional open large incision used for surgical entry. Typically, a surgeon inserts a needle attached to a suture through an access port using a needle holding instrument, passes the needle through a portion of severed or non-severed internal tissues at an internal surgical site, and makes a knot in the suture using a grasping instrument extending through a second access port and the needle holding instrument. One of these instruments is replaced with a cutting instrument to cut the needle off the suture so that it can be taken out.

These skills are difficult to learn and tying the knot is particularly challenging. The knot can be too loose, too tight, and tear out of the tissues if improper tension is placed on the suture when tying the knot. Furthermore, the needle can get lost inside the patient's body if it breaks off the suture when the knot is being tied or if it drops off the instrument when it is being taken out of the access port.

To alleviate this difficulty, a multitude of knot pushers are available that transfer a knot tied outside the patient's body (extracorporeal) to the surgical site inside the body (intracorporeal) through the access port. In a typical surgical procedure using a knot pusher, the suture is stitched between two portions of a severed or non-severed tissue with both ends of the suture extending out of the access port. The surgeon ties the suture into a slidable knot extracorporeally and a working end of a knot pusher is placed behind the knot. The knot pusher's working end is pushed against the knot while the surgeon pulls on both ends of the suture with equal tension in the opposite direction. This transfers the knot down the access port and tightens it at the surgical site. These steps can be repeated so that a plurality of knots can be placed.

U.S. Pat. No. 3,871,379 to Clarke (1975) describes a knot pusher with a C-shaped working end that captures and slides the knot to the surgical site where it is tightened by pulling on the suture ends. Although this device can transfer the knot, the knot rests deeply within the working (distal) end of the knot pusher and this can hinder the knot from being cinched tightly against the tissue. In addition, the knot can drop off, slide sideways out of position, and jam at the working end.

A number of knot pushers have a working end with a groove, a notch, a cut-out, and a slot that transfer and tighten the knot directly against the tissue. For example, U.S. Pat. No. 2,595,086 to Larzelere (1952) discloses a grooved ring, U.S. Pat. No. 5,234,444 to Christoudias (1993) shows a pusher with a pair of grooves, U.S. Pat. No. 5,403,330 to Tuason (1995) demonstrates a plurality of cut-outs, U.S. Pat. No. 5,201,744 to Jones (1993) has a notch and a magnetized slot, U.S. Pat. No. 5,549,618 to Fleenor et al. (1996) shows a slotted knot pusher assembly, U.S. Pat. No. 5,217,471 to Burkhart (1993) describes a recessed notched guide and a jawed knot holder, and U.S. Pat. No. 6,221,084 to Fleenor (2001) discloses a notched sleeve at the working end. Although these knot pushers can transfer the knot directly against the tissue, the knot may drop off, lock up, or slide sideways off the working end.

A number of knot pushers have a hook, an eyelet, a slot, or a groove that encircle and hold the suture at a working end to minimize the problem of dropping the knot. However, their designs have numerous disadvantages. For example, U.S. Pat. No. 6,258,106 to Leonard (2001) describes a pusher with a slotted J-hooked working end and U.S. Pat. No. 6,045,561 to Marshall et al. (2000) show one with a slotted circular working end. Both devices releasably capture one end of suture, transfer the knot, and cinch it to the tissue. However, the knot tends to slide sideways off the working end.

U.S. Pat. No. 5,176,691 to Pierce (1993) discloses twelve different knot pushers. One device has a working end with a pair of suture holding eyelets and a face to push the knot, another has a cylinder with a pair of eyelets that slides on a rod, another has a pair of two elongated movable parts where each has an eyelet, another has a pair of elongated moving members where each has an eyelet, and another has a pair of grooves with a transverse hole to insert suture. Pierce states that binding and jamming of the knot may occur in the eyelets or holes so he recommends that the surgeon "apply tension alternately to the suture ends in a reciprocating, see-sawing, or jiggling motion." However, this can damage the suture or the knot. Also, the frictional forces between the knot and the face that pushes it can restrict knot transfer, damage the knot, and tear suture out of the surgical site. In addition, the surgeon rust take extra operating time to repetitively and tediously remove one end of suture out of an eyelet, tie the knot, and re-thread the suture in the eyelet for all knots subsequent to the first.

Pierce discloses two other devices that have either a pair of wedge-shaped bars or a rotating sleeve that open and close a pair of eyelets. However, these bars and sleeves can be difficult to operate, and can jam, damage, or cut the suture.

Pierce also discloses a knot pusher that has a ring that holds the suture in a pair of grooves. However, the knot may slide to the side, lock in the ring, or fall off the working end if the ring dislodges or breaks. Another device has a removable working end and a mechanism to snap a suture in a pair of eyelets that can fall off inside a patient. Pierce describes two more devices that have a face and a number of eyelets, of which one has a hollow interior. Both are designed to push a knot sideways. However, they can be awkward to use, lock the knot, and difficult to place a tight knot. Another has a working end with a sliding suture cutting tube that can malfunction and inadvertently cut the knot or tissue.

U.S. Pat. No. 5,292,327 to Dodd et al. (1994), discloses a knot pusher with a concave eyelet that pushes the knot. However, the knot may lock, fray or break, and the suture can tear out of the tissue.

U.S. Pat. No. 5,324,298 to Phillips, et al. (1994) shows a knot pusher with a working end that has a slotted groove and a locking sleeve with a slit. Alignment of the slot, slit, knot, and suture can be difficult; and a tip that "bears against the slip-knot" may damage or lock the knot.

U.S. Pat. No. 5,423,837 to Mericle, et al. (1995) discloses a knot pusher with a working end that has a slotted hole that pushes against the knot that can become locked and a spring based suture-cutting shaft that can malfunction and inadvertently cut tissue.

U.S. Pat. No. 5,752,964 to Mericle (1998) describes a knot pusher with a flattened working end that has an eyelet between a pair of resilient opposing jaws with a spring based blade to cut suture where pulling on the suture as the sides of the jaws are pushed against the tissue tightens the knot. However, the knot can slide into the eyelet and lock in the jaws.

U.S. Pat. No. 5,797,929 to Andreas, et al. (1998) describes a shaft with a closable slot that pushes the knot. However, the knot can fall out of the slot if it opens or can lock in the slot during knot transfer.

U.S. Pat. No. 4,602,635 to Mulhollan et al. (1986) shows a knot pusher with a tunneled oblique flat working end and U.S. Pat. No. 5,269,791 to Mayzels et al. (1993) describes a knot pusher with a working end that has a spiraling coil and a terminal eyelet. Both devices cinch the knot by pulling the suture and pushing the working end against the knot. However, both devices can inadvertently lock the knot before it is fully transferred to the surgical site and tear the suture out of the tissue.

A number of knot pushers are designed where the suture is coiled around a working end, manipulated off the knot pusher, and tightened at the surgical site. For example, U.S. Pat. No. 5,397,326 to Magnum (1995) shows a pair of U-shaped clefts and a spiral channel to hold suture at an end of a knot pusher. Magnum states that suture may drop off the clefts or slip out of the channel of this device.

U.S. Pat. No. 5,741,280 to Fleenor (1998) demonstrates a more complicated knot pusher assembly where a knot carrier tube with concentric ferrules deploys knots that can tangle and tear the suture out of the tissue since both ends of suture are "tensioned to form a complete knotted loop."

Knot tiers comprised of complex mechanical moving parts have been described. U.S. Pat. No. 4,961,741 to Hayhurst (1990) discloses a suturing device where a leading member slides the first knot to the surgical site and opens to permit a trailing member to pass through it so that a second knot is placed.

U.S. Pat. No. 5,192,287 to Fournier (1993) discloses a complex mechanical device that has two shaft members, an actuation mechanism, and a set of suture holding grooves at the working end.

U.S. Pat. Nos. 5,084,058 (1992), 5,163,946 (1992) to Li, and U.S. Pat. No. 5,133,723 to Li, et al. (1992) describe a series of complex mechanical pegs for releasably supporting a plurality of knots, a knot rundown tool with a pair of grooves that has a slot for removing throws from the pegs, and a third device that blindly cuts the suture ends.

Although these devices are useful, the complex construction and moving parts make them more vulnerable to the effects of wear and tear that may result in breakage of parts where the device can stop working or leave broken metal pieces in the patient's body which must be retrieved. Furthermore, any malfunction of these devices during surgery can damage the suture, the knot, and the tissue being sutured.

In addition to knot pushers, knot pullers for intracorporeal knot tying have been devised. For example, U.S. Pat. No. 5,693,061 to Pierce et al. (1997) discloses a knot puller where a pair of appendages hold a length of suture between them and the knot is tied by the applying tension to the suture adjacent the knot. Applying tension can tear out the suture or damage the tissue being tied.

Thus, all prior art devices of extracorporeal knot pushers that I am aware of have one or more of the following disadvantages: (a) knots can drop off, slide to the side, and lock up in the working end; (b) knots or suture can fray and break from the frictional resistance between the suture or knot and the working end during knot transfer and tightening of the knot; (c) the suture can tangle intracorporeally and become difficult to tighten; (d) knots can be cinched loosely so that tissue approximation is unsatisfactory; (e) knots can be torn out of the tissue from pulling on the suture in the opposite direction from the tissue being sutured; and (f) due to complexity, they can break apart, stop functioning, or malfunction causing damage to the suture or knot, resulting in bodily injury, or requiring retrieval of broken parts.

BACKGROUND OF THE INVENTION—OBJECTS AND ADVANTAGES

Accordingly, several objects and advantages of the present invention are:

(a) to provide an improved knot transferring device;

(b) to provide such a device which can transfer a plurality of extracorporeally fashioned slidable knots individually and tighten them with precision and dispatch with and without pause to an intracorporeal surgical site through an access port with a minimal amount of tension on the free ends of the suture;

(c) to provide such a device where knots do not drop off, slide to the side, or lock up in the working end;

(d) to provide such a device where knots and suture do not tend to fray or break from frictional resistance between the suture or knot and the working end during knot transfer and tightening;

(e) to provide such a device where suture does not tangle intracorporeally or become difficult to tighten;

(f) to provide such a device where knots may be cinched so that tissue approximation is optimal;

(g) to provide such a device where pulling on the suture in the opposite direction from the tissue being sutured is minimized so that knots are not torn out of the tissue; and (h) to provide such a device that does not have any moving parts so that malfunction is less likely to occur as compared to those that are more complex.

Further objects and advantages will become apparent from consideration of the ensuing description and the accompanying drawings.

SUMMARY OF THE INVENTION

In accordance with the present invention, a knot placer comprises an elongated straight cylindrical rod that has a handle at one end and a pair of legs at the other (working end) for transferring and tightening a slidable knot from outside to inside a patient's body through an access port during an endoscopic surgery. The pair of legs is rectangular in shape and perpendicular to the end of the rod. Each has an eyelet or center hole, of which one has a slit, where each eyelet holds an end of a suture on either side of the knot. Pushing the handle and holding the ends of the suture transfers the knot through the access port to an internal surgical site where the knot is tightened. After the knot is tightened and the knot placer is withdrawn from the access port, the slit facilitates removal of one end of the suture out of the slit eyelet so that another knot can be tied, the suture quickly replaced in the eyelet through the slit, and the knot placed at the surgical site. This procedure can be done quickly and repetitively so that a plurality of knots can be placed one at a time.

DRAWINGS—FIGURES

DRAWINGS—REFERENCE NUMERALS

Figure 1:
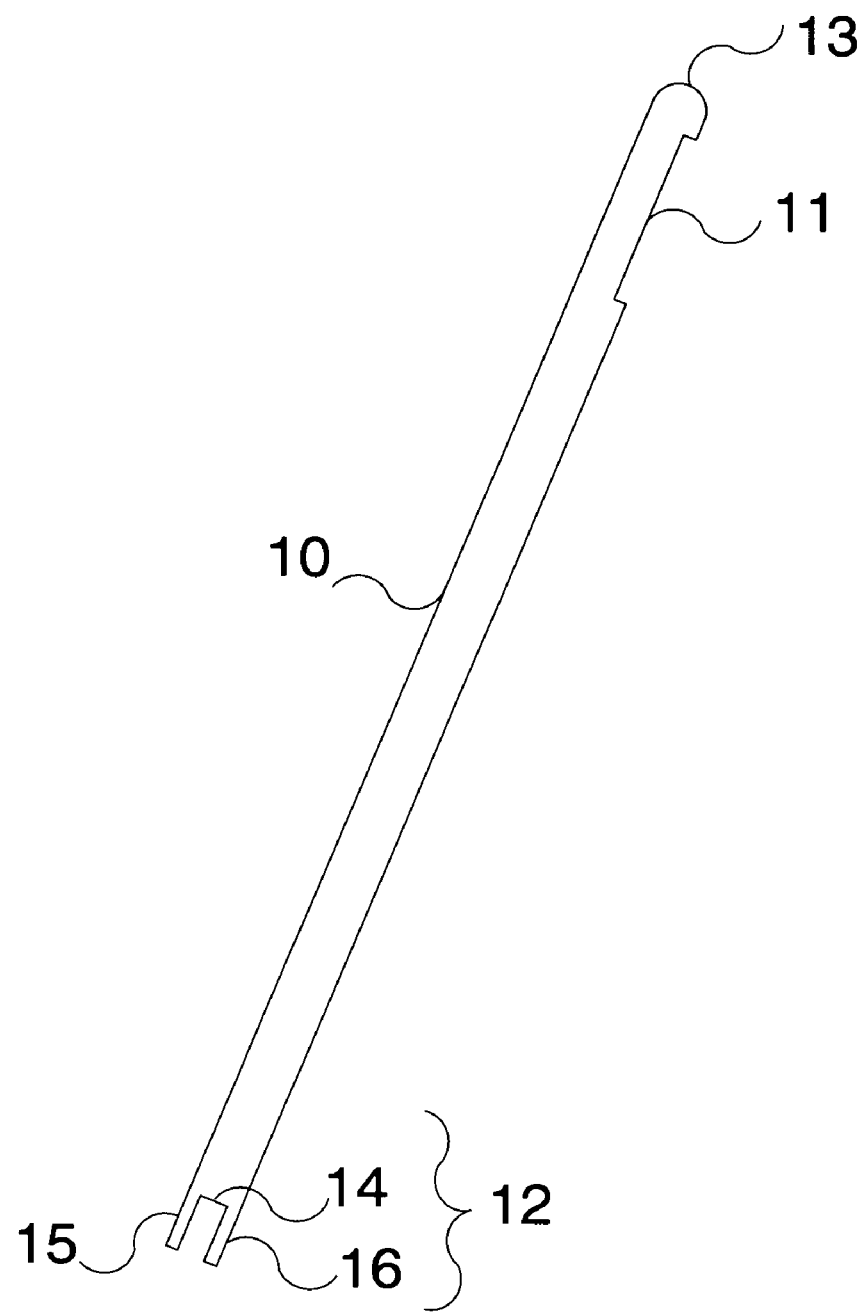
FIG. 1 is a perspective view of a knot placer according to one preferred embodiment of the present invention.
Figure 2A:
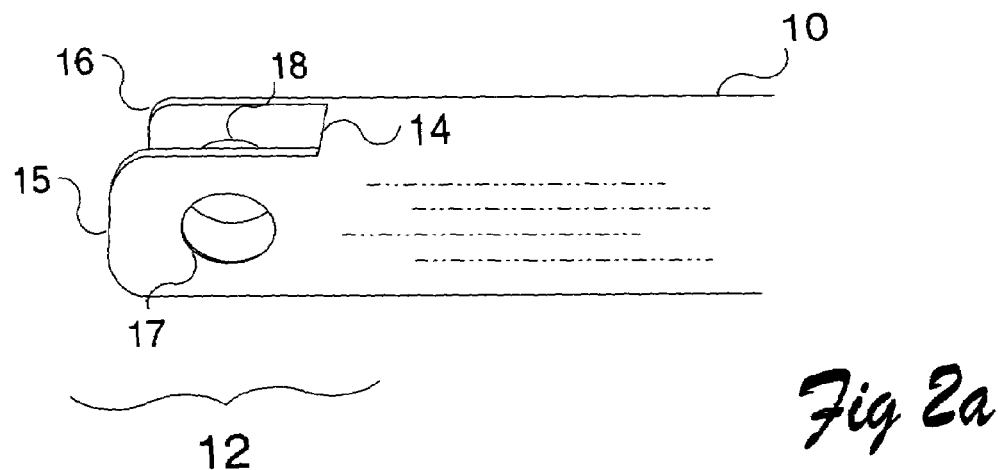
FIG. 2a is a perspective view of an eyelet of a working end of the knot placer of FIG. 1.
Figure 2B:
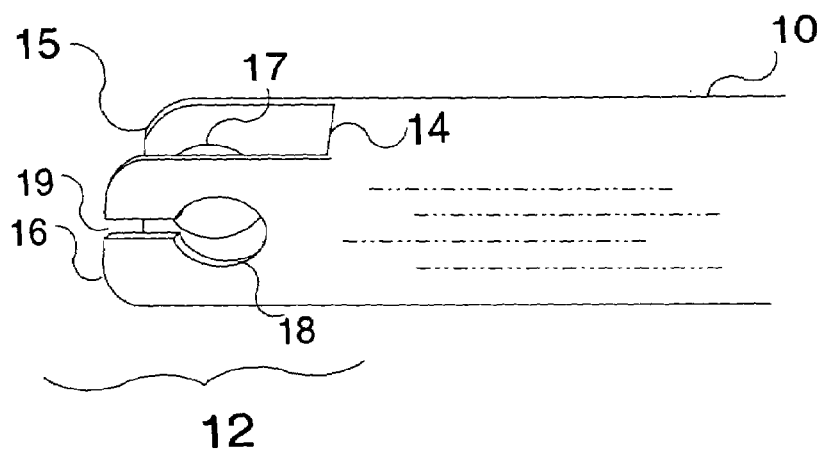
FIG. 2b is a perspective view of a slit eyelet of the working end of the knot placer of FIG. 1.

10 Rod
11 Handle
12 Working end
13 Round end of rod
14 Flat end of rod
15 Leg with closed eyelet
16 Leg with slit eyelet
17 Closed eyelet
18 Slit eyelet
19 Slit
20 Patient's skin
21 Access port
22 Patient's body cavity
23 Open proximal end of access port
24 Open distal end of access port
25a End of surgical suture
25b Other end of surgical suture
26 Patient's tissues at internal surgical site
27 Slidable knot DETAILED DESRIPTION—FIGS. 1-2b—PREFERRED EMBODIMENT A preferred embodiment of a knot placer for transferring and tightening a slidable knot on a suture from outside to inside a patient's body during an endoscopic surgery is illustrated in FIG. 1. The knot placer is a straight member, approximately 60 cm in length, and constructed of stainless steel that may be manufactured through methods well known in the art. The knot placer consists of a rod or middle part 10, a handle 11, and a working end 12. Rod 10 has a round proximal end 13, a flat distal end 14, and measures approximately 59.6 cm×4 mm (cylindrical shape). Handle 11 is a slot measuring roughly 10 cm×3 mm×0.75 mm (rectangular shape) and is approximately 3 cm from round end 13.

FIGS. 2a-b show details of working end 12 which consists of two tires or legs 15 and 16. Leg 15 (FIG. 2a) has a closed eyelet 17 and leg 16 (FIG. 2b) has a slit eyelet 18. Leg 15 has approximate overall dimensions 4 mm×4 mm×1 mm (square shape with rounded corners). Its closed eyelet or center hole 17 (round shape) has a diameter roughly 2 mm (FIG. 2a). Leg 16 has approximate overall dimensions of 4 mm×4 mm×1 mm (square shape with rounded corners) and its slit eyelet or center hole 18 (round shape) has a diameter roughly 2 mm. Eyelet 18 has a slit 19 (rectangular shape) having overall approximate dimensions of 1 mm×1 mm (FIG. 2b). Legs 15 and 16 are parallel to each other, and perpendicular to flat end 14. Handle 11 and leg 16 are parallel to each other and on the same side of rod 10.

Figure 3:
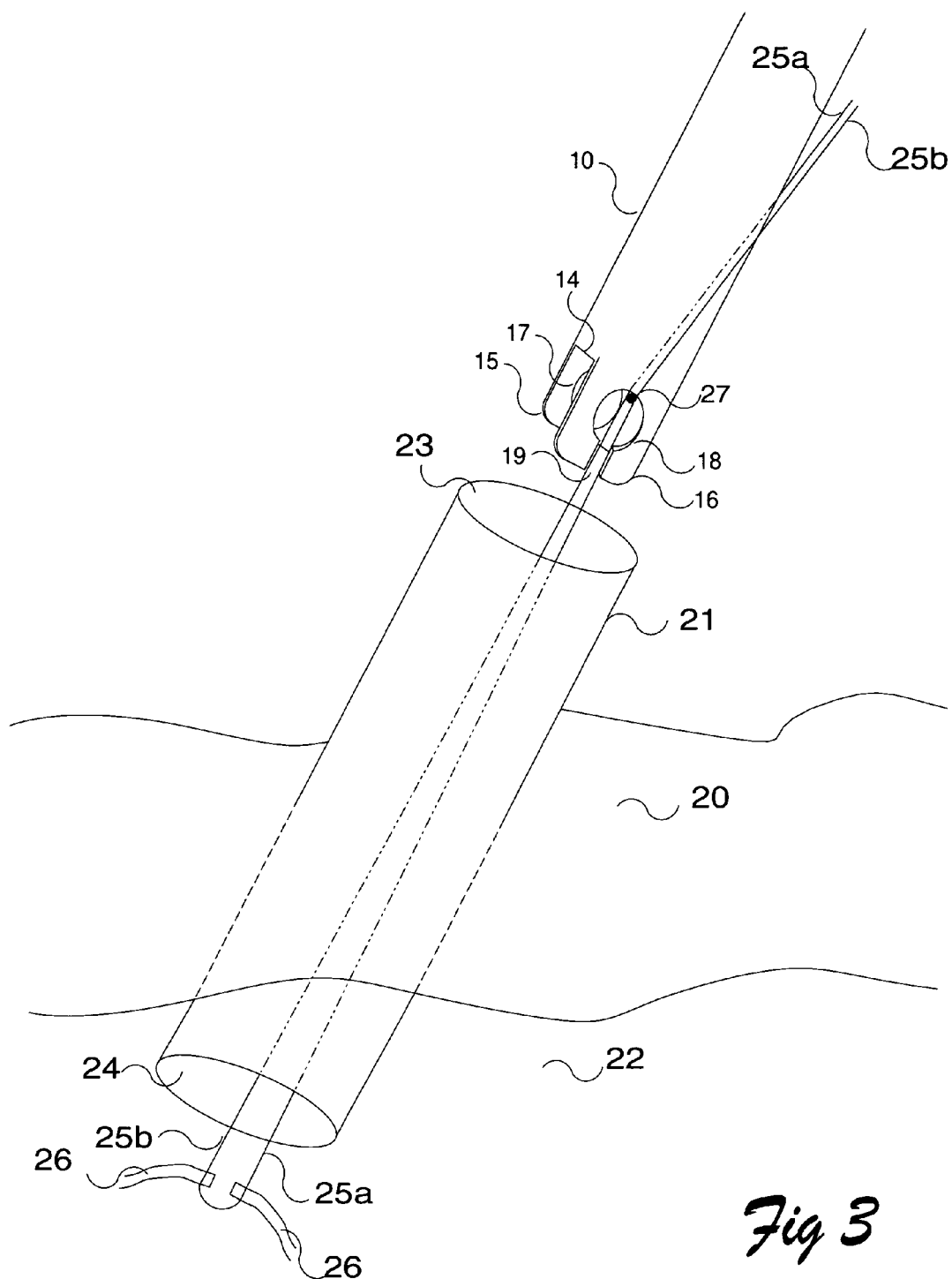
FIG. 3 is a perspective view of the knot placer applied to a slidable knot outside a patient'3 body according to the preferred embodiment of FIG. 1.

Operation—FIG. 3

Typically, a surgeon performs endoscopic procedures such as laparoscopy, pelviscopy, thoracoscopy, and arthroscopy through a number of small incisions in a patient's skin 20, each of which has a hollow tube or conventional access port 21 inserted in a patient's body cavity 22 for surgical access. Access port 21 is usually 5 mm, 12 mm, or 15 mm in diameter, has an open proximal end 23, and an open distal end 24. End 23 is thus outside skin 20 and end 24 is inside body cavity 22, respectively. A control device (not shown) located inside access port 21 near end 23 provides an air and water tight seal so that an instrument such as an endoscopic camera (not shown), also known as an "endoscope," or the knot placer can be placed though patient's body cavity 22 via access port 21 without causing gas or fluid to leak from it as generally used for endoscopic procedures.

Assume that a slidable knot is tied extracorporeally from a pair of suture ends 25a and 25b outside skin 20 and that this knot must be transferred inside body cavity 22 to join a patient's tissues at an internal surgical site 26. Specifically, the surgeon attaches one of suture end 25a or 25b to a needle (not shown). A surgical suture manufacturer can also attach the needle to suture end 25a or 25b using methods well known in the art so that it can be used by the surgeon. The surgeon then holds the needle with a conventional needle holding instrument (not shown).

The surgeon advances the needle down access port 21, through patient's tissues at internal surgical site 26, and then brings it out of access port 21. The needle is then cut off and discarded.

The surgeon ties slidable knot 27 extracorporeally through methods well known in the art using suture ends 25a and 25b. Then, the surgeon holds suture ends 25a and 25b side-by-side horizontally so that they are not crossed above or below the knot. The surgeon should be skilled in tying one-handed knots with this hand using methods well known in the art.

Next, second hand (instrument hand) grasps handle 11 of the knot placer so that its handle 11 and leg 16 are closer to the surgeon's body, and working end 12 is closer to end 23 of access port 21. The surgeon then holds the knot placer and suture ends 25a and 25b so that they are side-by-side horizontally. Handle 11 and leg 16 are parallel and on the same side of rod 10 so that the surgeon can properly position the knot placer in a darkly lit room as generally used for endoscopic procedures.

Next, the knot tying hand threads suture end 25a or 25b, whichever is closest to the knot placer, between legs 15 and 16 and through closed eyelet 17 of leg 15 while slidable knot 27 and eyelet 17 are still outside the patient's body. The surgeon then passes the other suture end 25*a* or 25*b* into slit eyelet 18 through slit 19 of leg 16. This is not shown in the drawings, but can easily be visualized. The surgeon then holds suture ends 25*a* and 25*b* side-by-side, horizontally, and directly underneath the knot placer so that there is no slack, and they are not crossed above or below the knot.

The surgeon pushes the knot placer toward slidable knot 27 so that suture ends 25*a* and 25*b* slide through eyelet 17 of leg 15 and eyelet 18 of leg 16. The surgeon then carefully pushes the knot placer as close to slidable knot 27 as possible so that it is centered between legs 15 and 16 and not advanced into access port 21 (FIG. 3).

Figure 4:
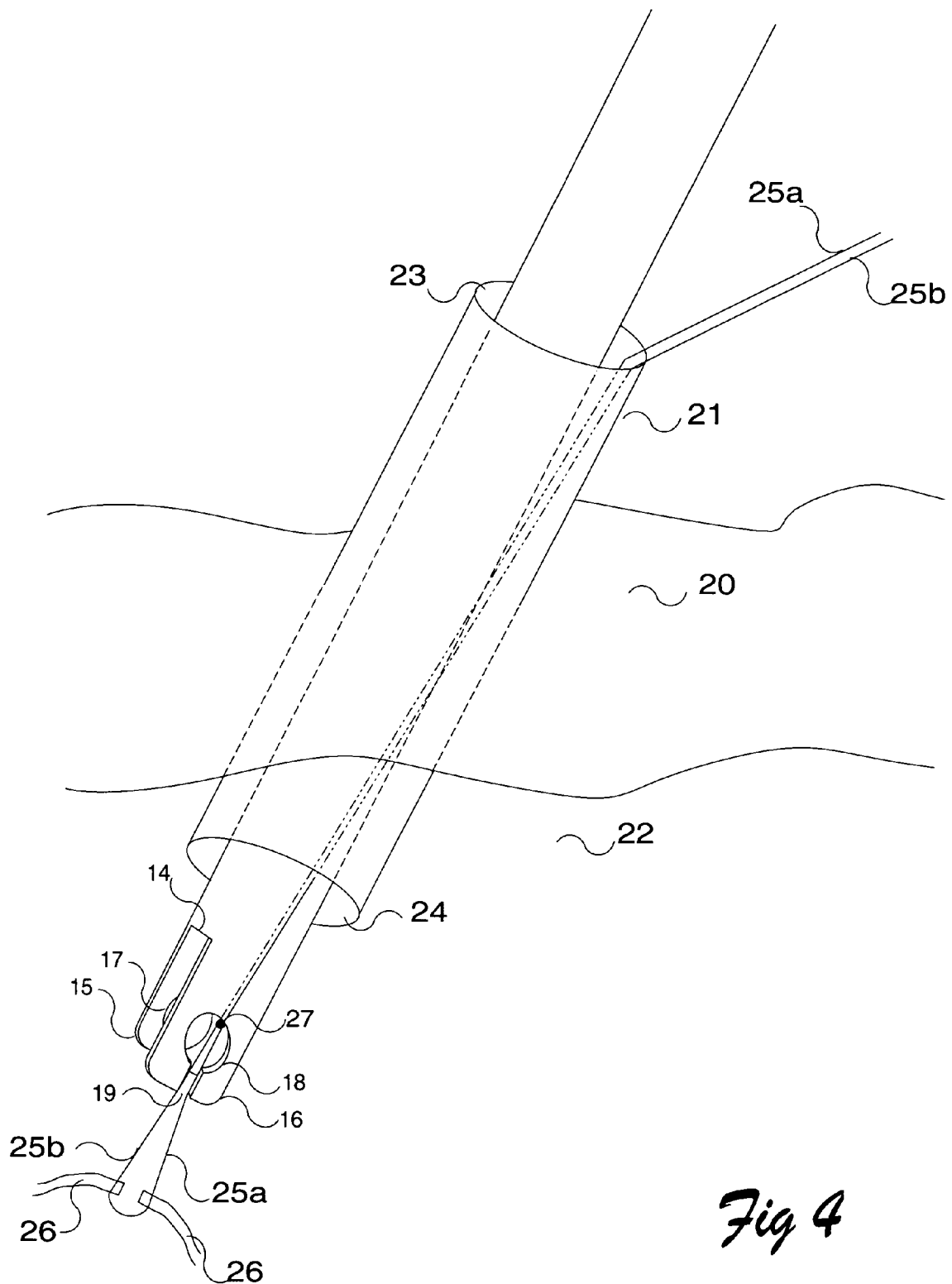
FIG. 4 is a perspective view of the knot placer applied to the slidable knot transferred into the patient's body through an access port joining a pair of internal tissues according to the preferred embodiment of FIG. 1.

Next, the surgeon aligns the knot placer, access port 21, and internal surgical site 26 in a straight line; a position called "the starting position for knot transfer." The surgeon then inserts working end 12 of the knot placer into end 23 of access port 21. He or she then pushes the knot placer down access port 21 so that it transfers slidable knot 27 down to internal surgical site 26 (FIG. 4). Eyelets 17 and 18 enable threaded suture ends 25*a* and 25*b* to slide as slidable knot 27 is transferred down to internal surgical site 26. The surgeon then pushes working end 12 of the knot placer and slidable knot 27, centered between legs 15 and 16, directly against the patient's tissues at internal surgical site 26 so that it causes slidable knot 27 to tighten and join the tissues through which the needle was passed. The surgeon then pulls the knot placer away from slidable knot 27 so that it does not loosen and suture end 25*a* or 25*b* passes out of slit eyelet 18 through slit 19 of leg 16. Finally, the surgeon completely withdraws the knot placer out of access port 21 without rotating it or removing suture end 25*a* or 25*b* from eyelet 17.

The knot placer is generally used to transfer and tighten two or more slidable knots 27. Thus, the surgeon releases suture ends 25*a* and 25*b*. Eyelet 17 of leg 15 holds its respective suture end 25*a* or 25*b* so that it does not fall off working end 12 of the knot placer.

Next, the knot tying hand holds rod 10 of the knot placer so that its orientation does not change. The instrument hand then releases handle 11 and holds rod 10 of the knot placer and suture end 25*a* or 25*b* threaded through closed eyelet 17 of leg 15.

Next, the knot tying hand ties a second one-handed slidable knot (not shown). Then, the knot tying hand holds rod 10 of the knot placer and threaded suture end 25*a* or 25*b* threaded through closed eyelet 17 of leg 15 so that the instrument hand can release the knot placer.

Next, the instrument hand grasps handle 11 of the knot placer so that its handle 11 and leg 16 are still closer to the surgeon's body. Then, the knot tying hand releases only rod 10 and holds suture ends 25*a* and 25*b* side-by-side, horizontally, and directly below the knot placer without slack. The surgeon then pushes the knot placer so that suture end 25*a* or 25*b* slides through closed eyelet 17 of leg 15 and the knot placer comes as close as possible to the second slidable knot without advancing it into access port 21. The surgeon then replaces removed suture end 25*a* or 25*b* conveniently back into slit eyelet 18 through slit 19 of leg 16 so that suture ends 25*a* and 25*b* are not crossed above or below the second slidable knot. The surgeon then aligns the knot placer, access port 21, and internal surgical site 26 so that they assume the starting position for knot transfer.

Then, the knot placer transfers and tightens the second slidable knot at internal surgical site 26 as previously described. Eventually, the knot placer transfers and tightens a final slidable locking knot (not shown) at internal surgical site 26 so that it locks the last placed slidable knot (not shown) through methods well known in the art.

Finally, the knot placer is withdrawn out of access port 21, suture ends 25*a* and 25*b* are removed from working end 12, and the knot placer is set aside. A conventional endoscopic scissors (not shown) is inserted down access port 21 and is used to cut suture ends 25*a* and 25*b* near the final slidable locking knot. The knots and other parts of the sutures will either dissolve and be absorbed by the body in a few days to months or be permanent and not absorbed over time.

In the unlikely event that suture end 25*a* or 25*b* falls accidentally out of slit eyelet 18 of leg 16 during transfer of slidable knot 27, the surgeon withdraws the knot pusher outside access port 21 without unthreading suture end 25*a* or 25*b* from eyelet 17 of leg 15. The surgeon then replaces dropped suture end 25*a* or 25*b* into eyelet 18 through slit 19 of leg 16, advances the knot pusher to slidable knot 27, the last placed slidable knot, or locking knot to transfer and tighten it at patient's tissues at internal surgical site 26.

CONCLUSIONS, RAMIFICATIONS, AND SCOPE

Accordingly the reader will see that, according to the invention, I have provided a knot placer with a working end where a plurality of extracorporeally fashioned slidable knots are individually transferred and tightened with precision and dispatch with and without pause to an intracorporeal surgical site through a conventional access port with a minimal amount of tension on a pair of suture ends. Importantly, the knot placer can be used to advance the knot as slack is taken up in the pair of suture ends without pulling on them. Furthermore, the working end of my knot pusher places tensile forces on the suture nearest the slidable knot in a direction roughly perpendicular to the axis of the rod and the knot, rather than by exerting parallel forces. Therefore, the knot slides easily because friction and resistance is minimal. In addition, my knot placer prevents the slidable knot from dropping off the working end because one suture end remains in an eyelet at all times. In addition, my knot placer prevents the knot from sliding to the side of the working end because the knot rests between two legs, one with a closed eyelet and one with a slit eyelet. The slit of the eyelet is strategically located opposite the flat end of the rod so that the slit eyelet is least likely to drop its respective end of suture during knot transfer and tightening. In addition, the slit provides an opening so that the surgeon can rapidly release the respective end of suture from the slit eyelet leg after the knot is tightened. This enables the surgeon to tie a second one handed slidable knot, quickly insert the respective end of suture back into the slit eyelet, transfer the second knot into the patient's body, and tighten it at the internal surgical site to join internal tissues. Therefore, my knot placer swiftly transfers and tightens multiple slidable knots one at a time. Furthermore, my knot placer minimizes the potential for the slidable knot to lock up on the working end because each slidable knot rests between the legs and beyond the flat end of the rod so that contact of the knot and the working end is minimal. Also, my knot placer does not tangle the suture and the slidable knot is easy to tighten. In addition, the suture does not to fray or break because the holes of the eyelets have rounded smooth surfaces that minimize trauma to the suture. Furthermore, the suture is not torn out of the tissue being sutured because the pair of suture ends is not pulled in the opposite direction from the tissue at the surgical site. In addition, my knot placer has the capability to enable a surgeon to interrupt the knot transfer anytime before transfer is completed to the surgical site to assess surgical issues such as bleeding and tension on the tissues without fear of the knot dropping off the working end.

My knot placer also has a clearly shown capability to transfer and tighten a multiple intertwined slidable knot (surgeon's knot) with extreme ease to the surgical site, a feat that most other devices cannot accomplish. Only one surgeon is needed to use my knot placer, a distinct advantage over other devices that have multiple parts and where an assistant is needed for its preparation and function.

Another advantage of my knot placer is its simple construction, which makes it less likely to break or malfunction.

My knot placer is easy to maintain and clean. Cleaning of more complicated instruments can be difficult and time consuming since they require a thorough inspection to insure that they still function properly that crusted old blood is removed from the tiny recesses before sterilization and reuse.

While the above description contains many specificities, these should not be construed as limitations on the scope of the invention, but as exemplifications of the presently preferred embodiments thereof. Many other ramifications and variations are possible within the teachings of my invention. Modifications in a wide variety of ways to the precise dimensions, length, width, height, shape, and cross-sectional area of the legs, eyelets, slit, rod, and handle can be made and still fall within the spirit of my device. For example, the legs, eyelets, slit, rod, and handle can be triangular, oval, square, rectagonal, and other regular or irregular shape, and can transfer and tighten the slidable knot to the surgical site easily and safely without damaging the knot, the suture, and the tissue.

Although my knot placer can be used to tie knots to join and repair tissues that are severed such as a hole in a bladder or a cut in an intestine, it can also be used to unite and approximate tissues that are not severed as routinely done during surgery where the stomach is sutured around the esophagus to prevent the common problem of reflux of gastric contents into the esophagus (gastroesophageal reflux disorder).

Also, my knot placer can be reusable or disposable:

In addition, my knot placer can be used to transfer and tighten a slidable knot to areas of the body that are difficult to reach during open surgical operations that use large conventional open incisions for surgical access.

Furthermore, my knot placer can be used to transfer and tighten a slidable knot to a surgical site in a non-human animal as can be used by those skilled in the art of veterinary medicine.

My knot placer can be turned upside down so that the handle (proximal) end can be inserted through the access port to the internal surgical site so that the knot placer can be used alternatively as a blunt instrument that can divide, retract, and probe internal tissues, structures, and organs. For example, gentle sweeping motions of the elongated shaft with its rounded end can bluntly probe, safely divide, and non-traumatically push aside a multitude of non-vascularized connecting tissues surrounding a kidney to facilitate its removal. The slot can be rotated into positions that effectively hold a bridge of vascularized connective tissue, likely to bleed if bluntly divided, so that it can be cut sharply with a conventional endoscopic scissors that seals and cuts blood vessels.

Thus the scope of the invention should be determined by the appended claims and their legal equivalents, and not by the examples given.

I claim:

1. A knot transfer instrument for transferring, through an access port coming from a body cavity in an endoscopic surgery, a slidable knot of the type that is formed from a surgical suture, has a pair of suture ends extending therefrom, and joins a patient's tissue, comprising:

an elongated cylindrical shaft, having a proximal and distal end, said shaft capable of cradling the slidable knot at the distal end, said proximal and distal ends being spaced a predetermined distance apart, said distal end of said shaft, along the longitudinal portion of the shaft, having a flat surface on the outer circumference of the shaft and perpendicular to a longitudinal plane of the shaft wherein a pair of spaced parallel legs extend longitudinally from the distal end of said shaft at opposite sides of the flat surface and are perpendicular to the flat surface, the legs comprising proximal and distal ends and having a rectangular shape with rounded corners and edges, one of the legs having a rounded hole eyelet connected to a slit wherein the slit extends to the distal end of the leg and the other leg having a rounded hole eyelet without a slit, whereby each of said legs can be used to hold a respective suture end extending from said slidable knot, and said knot transfer instrument can be used to urge said slidable knot forward from outside to inside said body cavity through said access port with precision, ease, and dispatch with and without pause, and said eyelets can facilitate tightening said slidable knot to join said patient's tissue contiguously.

2. The knot transfer instrument of claim 1 wherein said knot transfer instrument comprises stainless steel material.

3. The knot transfer instrument of claim 1 wherein said proximal end comprises a slot of predetermined dimensions for enabling an operator to grasp, push, and pull said knot transfer instrument in and out of said body cavity via said access port.

4. The knot transfer instrument of claim 1 wherein said slit connected to said eyelet is in a portion of the leg opposite said flat surface.

5. The knot transfer instrument of claim 1 wherein the leg comprising said slit is parallel and located on the same side of the shaft as a slot of predetermined dimensions for enabling an operator to grasp, push, or pull said knot transfer instrument in and out of said body cavity via said access port.

6. A knot transfer instrument for advancing forward, in an endoscopic surgery, a slidable knot formed from a pair of surgical suture ends, that unite and join a person's internal tissues, via an access port coming from a person's body cavity to outside a person's skin, comprising:

an elongated straight cylindrical shaft having a proximal and distal end, the proximal end comprising a handle and the distal end capable of cradling said slidable knot, said proximal and distal ends being spaced a predetermined distance apart, said distal end of said shaft, along the longitudinal portion of the shaft, having a flat surface on the outer circumference of the shaft and perpendicular to a longitudinal plane of the shaft wherein a pair of spaced parallel legs extend longitudinally from the distal end of said shaft at opposite sides of the flat surface and are perpendicular to the flat surface, the legs comprising proximal and distal ends and having a rectangular shape with rounded corners and edges, one of the legs having a rounded hole eyelet connected to a slit wherein the slit extends to the distal end of the leg and the other leg having a rounded hole eyelet without a slit, whereby each said eyelet of said legs can be threaded by one end of said surgical suture following creation of said slidable knot, and said knot transfer instrument can advance and urge said slidable knot forward from outside to inside said person's body cavity through said access port with precision, ease, and dispatch with or without pause, will facilitate tightening said slidable knot to join said patient's severed and non-severed tissues in close approximation.

7. The knot transfer instrument of claim 6 wherein said knot transfer instrument comprises stainless steel material.

8. The knot transfer instrument of claim 6 wherein said handle comprises a slot of predetermined dimensions for enabling an operator to grasp, push, and withdraw said knot transfer instrument in and out of said person's body cavity through said access port.

9. The knot transfer instrument of claim 6 wherein said proximal and distal ends of said shaft has a rounded surface.

10. The knot transfer instrument of claim 6 wherein said slit connected to said eyelet is in a portion of the leg opposite said flat surface.

11. The knot transfer instrument of claim 6 wherein the leg comprising said slit is parallel and located on the same side of the shaft as a slot of predetermined dimensions for enabling an operator to grasp, push, or pull said knot transfer instrument in and out of said body cavity via said access port.

* * * * *